(12) United States Patent
Carli et al.

(10) Patent No.: US 7,060,099 B2
(45) Date of Patent: Jun. 13, 2006

(54) DISK PROSTHESIS FOR CERVICAL VERTEBRAE WITH CONTROLLED CLEARANCE

(75) Inventors: Olivier Carli, Geneve (CH); Mourad Ben-Mokhtar, Paris (FR)

(73) Assignee: Scient' X, Guyancourt (FR)

( * ) Notice: Subject to any disclaimer, the term of this patent is extended or adjusted under 35 U.S.C. 154(b) by 0 days.

(21) Appl. No.: 10/673,165

(22) Filed: Sep. 30, 2003

(65) Prior Publication Data

US 2004/0267364 A1   Dec. 30, 2004

(30) Foreign Application Priority Data

Jun. 26, 2003   (FR) .................................. 03 07726

(51) Int. Cl.
*A61F 2/44* (2006.01)
(52) U.S. Cl. .................................................. 623/17.14
(58) Field of Classification Search ............. 623/17.11, 623/17.12, 17.13, 17.14, 17.15, 17.16
See application file for complete search history.

(56) References Cited

U.S. PATENT DOCUMENTS

| | | | | |
|---|---|---|---|---|
| 4,759,769 | A * | 7/1988 | Hedman et al. | 623/17.13 |
| 5,314,477 | A * | 5/1994 | Marnay | 623/17.15 |
| 5,401,269 | A * | 3/1995 | Buttner-Janz et al. | 623/17.15 |
| 5,562,738 | A * | 10/1996 | Boyd et al. | 623/17.15 |
| 5,676,701 | A * | 10/1997 | Yuan et al. | 623/17.15 |
| 5,895,428 | A * | 4/1999 | Berry | 623/17.15 |
| 5,899,941 | A * | 5/1999 | Nishijima et al. | 623/17.15 |
| 6,368,350 | B1 * | 4/2002 | Erickson et al. | 623/17.14 |
| 6,517,580 | B1 * | 2/2003 | Ramadan et al. | 623/17.15 |
| 6,679,915 | B1 * | 1/2004 | Cauthen | 623/17.11 |

* cited by examiner

*Primary Examiner*—Kevin Shaver
*Assistant Examiner*—Annette Reimers
(74) *Attorney, Agent, or Firm*—Clark & Brody

(57) ABSTRACT

A disk prosthesis includes first and second plates (2, 3) to be fixed on neighboring cervical vertebrae and an articulation arrangement (7) inserted between the two plates in a superposed position. The articulation arrangement allows for flexion-tension movements in a sagittal plane (S) according to a limited clearance, lateral inflexion movements in a plane perpendicular to the sagittal plane (S) according to limited angular clearance, and relative rotation movements between the first and second plates according to a limited angular clearance. The first and second plates are assembled to form a prosthesis of a single piece.

9 Claims, 3 Drawing Sheets

DISK PROSTHESIS FOR CERVICAL VERTEBRAE WITH CONTROLLED CLEARANCE

FIELD OF THE INVENTION

The purpose of the invention concerns a disk prosthesis for cervical vertebrae intended for substitution for the fibro-cartilaginous disk providing the connection between the cervical vertebrae of the spinal column.

BACKGROUND ART

It is known that an intervertebral disk may undergo changes such as compression, deformation, shift or wear and, more generally, degeneration associated with mechanical stress on it and leading to anatomic and functional destruction of the vertebral disk and segment. This disk alteration modifies the mechanical behaviour of the disk and results in a reduction in the height of the intersomatic space, in turn perturbing the functional articular unit. This results in instability, in particular inducing an arthrosis reaction, a source of pain and osteophytic processes. In the same way, nucleus pulposus herniation may arise, requiring the removal of the cervical disk.

Therefore, a proposal was made to replace the defective disk with an artificial disk and several types have been considered. For example, in particular U.S. Pat. No. 5,562,738 a disk prosthesis for lumbar vertebrae comprising first and second fixation plates to neighbouring vertebrae, made of a metal such as titanium. An articulation knob is inserted between the plates, comprising a first insert assembled on one of the plates and consisting of a spherical cap co-operating with a spherical cup from a second insert assembled on the other plate. The inserts are made of a biocompatible ceramic presenting improved tribology characteristics, in particular as regards the capacity of resistance to wear.

However, such a disk prosthesis for lumbar vertebrae is not suitable to replace the disk of cervical vertebrae since such a prosthesis does not allow the cervical vertebrae to recover their natural mobility. In addition, the shape of the articulation knob is relatively difficult to produce properly and is sensitive to break and crack phenomena, thereby reducing the life of the prosthesis.

Therefore, the purpose of the present invention is to rectify the disadvantages of the prior art by proposing a disk prosthesis for cervical vertebrae designed to present a relatively long life span by being practically insensitive to wear and break phenomena, while being adapted to authorise physiological mobility between the two equipped cervical vertebrae.

SUMMARY OF THE INVENTION

To reach such a goal, the prosthesis for cervical vertebrae according to the invention comprises:
  a first and second plate intended to be fixed on neighbouring cervical vertebrae,
  and means of articulation inserted between the two plates placed in a superimposed position.
  According to the invention, the means of articulation comprise:
    means authorising flexion-extension movements in the sagittal plane according to an angular clearance limited by stop means in flexion-extension,
    means authorising lateral inflexion movements in a plane perpendicular to the sagittal plane according to an angular clearance limited by stop means in lateral inflexion,
    means authorising relative rotation movements between the first and second plates according to an angular clearance limited by stop means in relative rotation,
    means of assembly with the first and second plates so as to form a prosthesis consisting of a single piece.
  According to a characteristic of the invention, the means of articulation comprise:
    a hole with a partially spherical profile established inside a chamber prepared in a plate,
    and a bearing surface with a profile complementary to the hole prepared in the other plate and assembled in the hole to be locked in the latter.

According to a first variant of the invention, the means authorising flexion-extension movements comprise an axis extending in the sagittal plane by protruding on both sides of the bearing surface, in the clearances prepared in the second plate by opening up into the spherical hole.

Preferably, the clearances have a determined diameter to define the angular clearance of relative rotation movements between the first and second plates.

According to a second variant of the invention, the means of stop in relative rotation consist of a female geometric shape co-operating with a complementary male geometric shape, one of the geometric shapes is prepared on the first plate while the other geometric shape is prepared on the second plate.

Advantageously, the means of stop in lateral inflexion consist of plate profiles entering into contact with each other.

Advantageously, the bearing surface is prepared in a first insert assembled on the first plate and made in the form of a stub and in that the hole is prepared in a second insert assembled on the second plate and made in the form of a ring.

Preferably, the inserts are made of ceramic or metal.

Miscellaneous other characteristics are derived from the following description with reference to the appended drawings, indicating, by way of non-limiting examples, different forms of the invention.

DESCRIPTION OF PREFERRED EMBODIMENTS

As more specifically indicated in the figures, the purpose of the invention concerns a disk prosthesis 1 to be implanted in the place of a disk between two adjacent cervical vertebrae. Cervical prosthesis 1 according to the invention comprises a first so-called upper plate 2 in the illustrated example and a second so-called lower plate 3. Plates 2 and 3 are intended to be fixed on neighbouring cervical vertebrae and each present an outer side, respectively $2_1$, $3_1$, of roughly similar dimensions adapted to take the exact shape of the associated articular surfaces.

Figure 1:
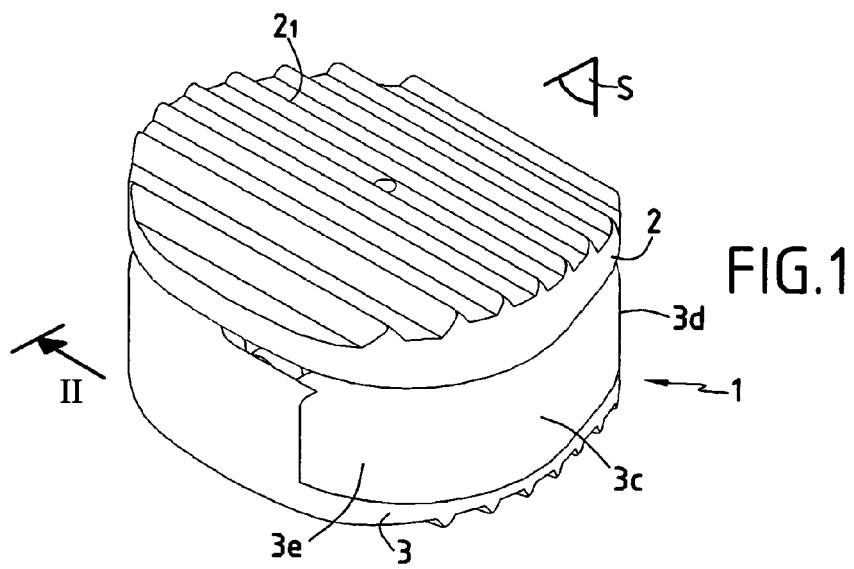
FIG. 1 is a perspective view showing a first example of a prosthesis complying with the invention.
Figure 2:
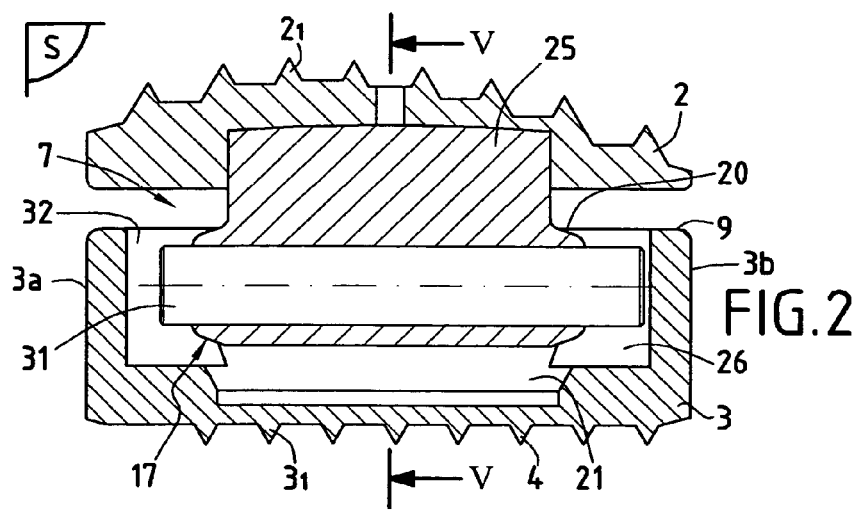
FIG. 2 is a front cutaway view roughly taken in the sagittal plane according to lines II—II in FIG. 1.

In accordance with the invention, plates 2 and 3 present an anatomic profile that can be adapted to the intervertebral space. Therefore, as indicated more specifically in FIG. 2, the first plate 2 presents a convex profile in the sagittal plane S, while the second plate 3 presents a roughly flat profile in the same sagittal plane S. Moreover, as more specifically indicated in FIG. 4, the second plate 3 has a convex profile in the front plane F, while the first plate 2 has a flat profile. Preferably, outer sides $2_1$, $3_1$ of plates 2 and 3 are equipped with bone anchoring elements 4 in the vertebrae. In the example illustrated in FIG. 1 to 3, outer sides $2_1$ and $3_1$ comprise parallel notches as anchoring elements 4 between themselves and the front plane F.

Figure 3:
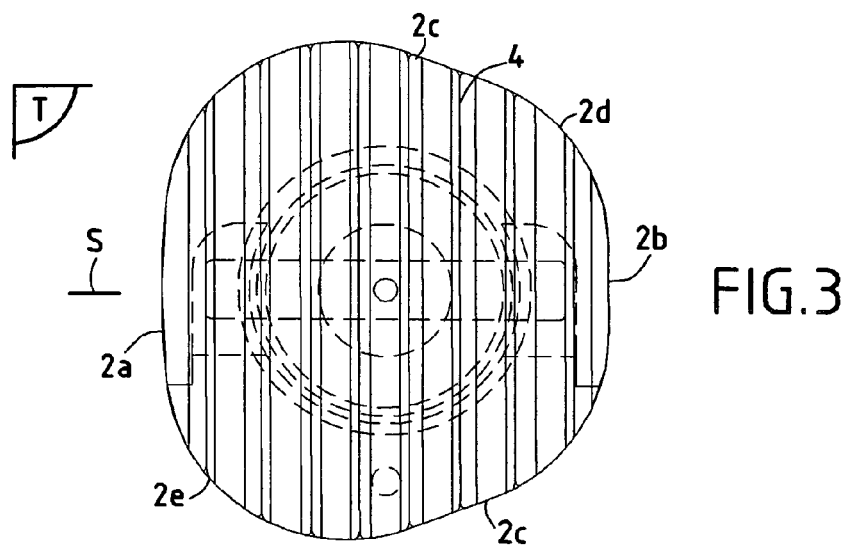
FIG. 3 is a horizontal projection of the prosthesis illustrated in FIG. 1.
Figure 4:
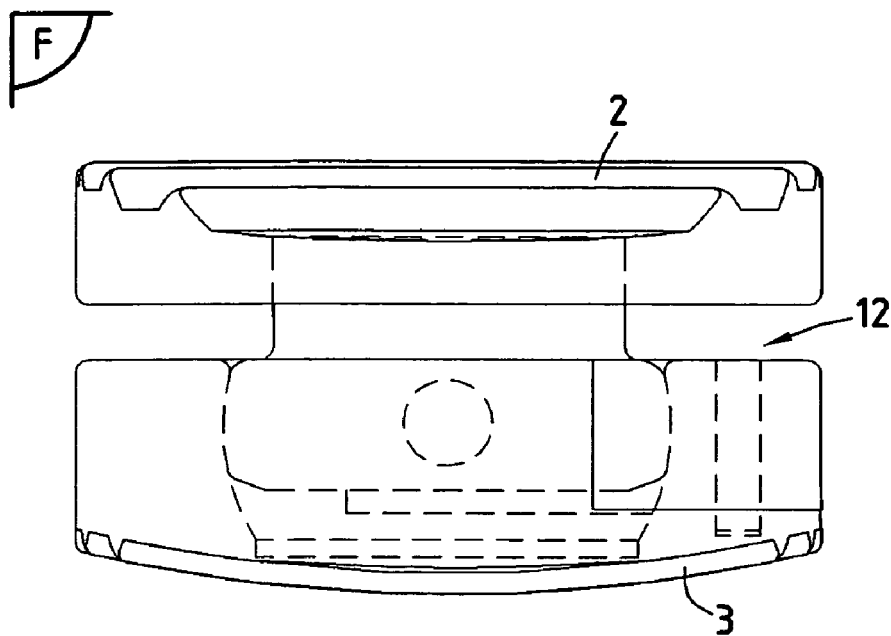
FIG. 4 is a front view of the prosthesis illustrated in FIG. 1.
Figure 5:
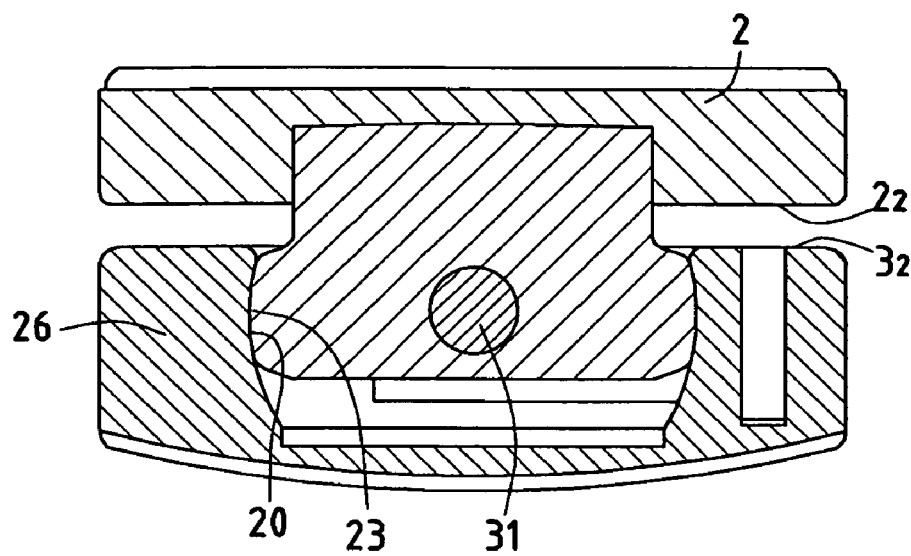
FIG. 5 is a front cutaway view taken roughly according to lines V—V in FIG. 2.
Figure 6:
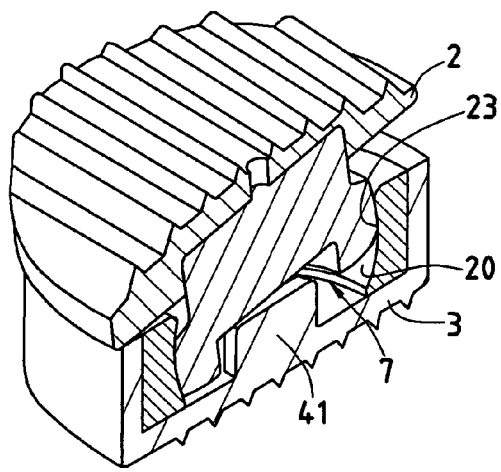
FIG. 6 is a partially cutaway view in perspective showing a second example of a prosthesis complying with the invention.

Advantageously, and as more specifically indicated in FIG. 3, each plate 2, 3 presents a general trapezoid form by having a posterior edge respectively 2a, 3a extending to the opposite side and parallel to front plane F and to an anterior edge 2b, 3b respectively. The anterior edge 2b, 3b of each plate 2, 3 is connected to the respective posterior edges 2a, 3a by means of two lateral edges 2c, 3c diverging from the anterior edge 2b, 3b. Preferably, each lateral edge 2c, 3c is connected to the respective anterior edge 2b, 3b by a connection fillet 2d, 3d as well as to the posterior edge 2a, 3a by means of a connection fillet 2e, 3e

According to the invention, means of articulation 7 are inserted between the two plates 2, 3 placed in a superimposed position. According to the invention, the means of articulation 7 consist of:

means authorising flexion-extension movements in the sagittal plane S according to an angular clearance limited by the means of stop in flexion-extension 9, means authorising lateral inflexion movements in a front plane F perpendicular to sagittal plane S according to an angular clearance limited by the means of stop in lateral inflexion 12, means authorising relative rotation movements between the first 2 and second 3 plates according to an angular clearance limited by the means of stop in relative rotation, means of assembly 17 with the first 2 and the second 3 plates so as to form a prosthesis consisting of a single piece.

As follows from the previous description, the means of articulation 7 enable control of the relative movements in the front plane F, in the sagittal plane S and in the cross plane T between the first 2 and second 3 plates according to limited movements corresponding to the natural physiological mobility between two cervical vertebrae. Of course, the means of articulation 7 allow that the plates can have movements according to the different combinations of these different planes.

The means of articulation 7, in particular, consist of a hole with a partially spherical profile 20, established inside a chamber 21 prepared in the illustrated example in the second plate 3. This hole is intended to co-operate with a bearing surface 23 with a profile complementary to hole 20. The bearing surface 23 with the partially spherical profile is assembled in hole 20 so as to be locked together. Bearing surface 23 is prepared in a first insert 25 assembled on the inner side of the first plate 2 and made in the form of a stub. In fact, as indicated in the figures, insert 25 includes a base with a circular cross-section partially inserted in a recess opening on to the inner side of plate 2. This base extends by bearing surface 23 with a partially spherical profile. Hole 20 is prepared in a second insert 26 assembled in chamber 21 of the second plate 3 and made in the shape of a ring. Inserts 25, 26 are made of metal or ceramic.

Hole 20 and bearing surface 23 are means authorising flexion-extension movements in the sagittal plane S, lateral inflexion movements in the front plane F, and relative rotation movements in the cross plane T.

The means of assembly 17 between the first and second plates 2, 3 are achieved by the insertion of the bearing surface 23 with a spherical profile in hole 20.

According to a first variant of the invention illustrated in FIG. 1 to 5, the means of articulation 7 comprise an axis 31 crossing the bearing surface 23 from one end to the other by extending in the sagittal plane S. Axis 31 protrudes on both sides of the bearing surface 23 by being engaged in the clearances 32 formed in the ring 26 by opening up in hole 20. The two clearances 32 that extend in a diametrically opposite way present a height, that is, a measurement in the sagittal plan S adapted to allow for flexion-extension movements in the sagittal plane of plate 2 relative to plate 3. The means of stop in flexion-extension are formed by the profile of plates 2, 3, coming into contact with each other.

According to another advantageous characteristic of the invention, clearances 32 has a determined diameter, that is, a measurement in the cross plane T determined to define the angular clearance of relative rotation movements between plates 2, 3. In fact, clearances 32 limit the rotation of the axis 31 according to the cross plane T. Clearances 32 thereby form means of stop in relative rotation between plates 2, 3.

According to another advantageous characteristic of the invention, axis 31 allows for lateral inflexion movements in the front plane F perpendicular to sagittal plane S, of plate 2 relative to plate 3. The means of stop 12 in lateral inflexion are formed by the profile of plates coming into contact with each other. Thereby, plates 2, 3 come into contact with each other according to lateral inflexion movements according to their inner side respectively $2_2$ and $3_2$ extending opposite each other.

FIGS. 6 to 9 illustrate a second variant of the prosthesis 1 complying with the invention. This prosthesis has means of articulation 7 identical to those described above and for this reason comprises the same references. In this variant of the invention, bearing surface 20 is part of a ring 38 presenting a slot 39 allowing for the assembly of a bearing surface 23 by elastic deformation.

According to a second variant of the invention, the means of stop in relative rotation are formed by a female geometric shape 40 co-operating with a complementary male geometric shape 41. One of the geometric shapes is prepared on a plate while the other geometric shape is prepared on the other plate. In the illustrated example, the female geometric shape is prepared on insert 25 assembled in one piece with the first plate 2 while the complementary male geometric shape 41 extends from the back of the chamber 21 of the second plate 3.

These female 40 and male 41 geometric shapes are said to be complementary in that they authorise flexion-extension movements in the sagittal plane S, lateral inflexion movements in the front plane F, and relative rotation movements between the first and second plates. These geometric shapes 40 and 41 are adapted to form means of stop in relative rotation between plates 2 and 3 for a limited angular clearance.

Figure 7:
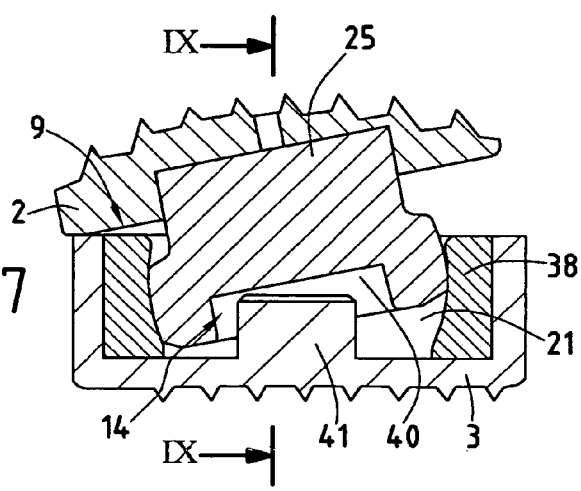
FIG. 7 is a front cutaway view taken in the sagittal plane of the prosthesis illustrated in FIG. 6.
Figure 8:
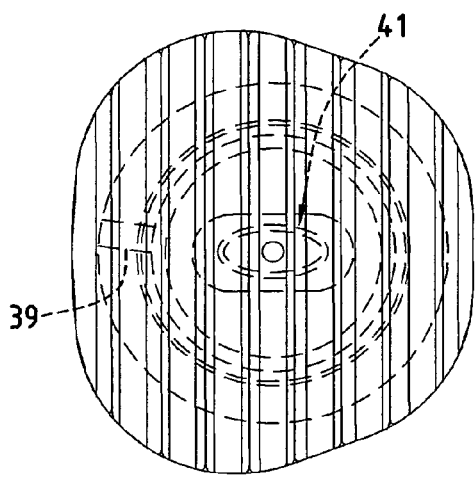
FIG. 8 is a top view of the prosthesis illustrated in FIG. 6.
Figure 9:
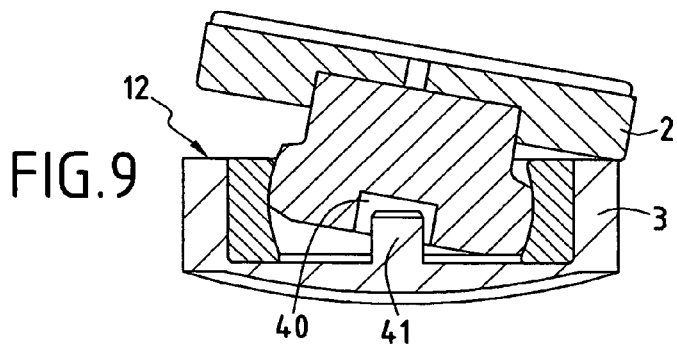
FIG. 9 is a front cutaway view taken roughly according to lines IX—IX—in FIG. 7.

The means of stop in flexion-extension are formed by the inner sides $2_2$, $3_2$ of the plates as more specifically indicated in FIG. 7. In addition, the means of stop in lateral inflexion 12 are formed by the inner sides respectively $2_2$ and $3_2$ of plates 2, 3 as indicated clearly in FIG. 9.

The invention is not limited to the examples described and represented since different modifications may be added without going beyond its scope.

What is claimed is:

1. Disk prosthesis for cervical vertebrae comprising:
   a first (2) and a second plate (3) intended to be fixed on neighboring cervical vertebrae, and
   a means of articulation (7) inserted between the two plates placed in superimposed position, characterized in that the means of articulation (7) further comprises:
   a means authorizing flexion-extension movements in a sagittal plane (S) according to an angular clearance limited by a means of stop in flexion-extension (9),
   a means authorizing lateral inflexion movements in a plane perpendicular to the sagittal plane (S) according to an angular clearance limited by a means of stop in lateral inflexion (12),
   a means authorizing relative rotation movements between the first (2) and second (3) plates according to an angular clearance limited by a means of stop in relative rotation,
   a means for assembling (17) the first (2) and second (3) plates so as to form a prosthesis consisting of a single piece.

2. Disk prosthesis according to claim 1, characterized in that the means of articulation (7) comprises:
   a hole (20) with a partially spherical profile established inside a chamber (21) prepared in the second plate, and a bearing surface (23) with a profile complementary to the hole (20) formed in the first plate and assembled in the hole (20) to be locked in the latter.

3. Disk prosthesis according to claim 2, characterized in that the bearing surface (23) is prepared in a first insert (25) assembled on the first plate (2) and made in the shape of a stub and that the hole (20) is prepared in a second insert (26) assembled on the second plate (3) and made in the shape of a ring.

4. Disk prosthesis according to claim 3, characterized in that the inserts (25, 26) are made of ceramic or metal.

5. Disk prosthesis according to claim 2, characterized in that the means authorizing flexion-extension movements comprises an axis (31) that extends in the sagittal plane (S) by protruding on both sides of a bearing surface formed in the first plate, and in clearances (32) prepared in the second plate by openings in a spherical hole of the second plate.

6. Disk prosthesis according to claim 1, characterized in that the means authorizing flexion-extension movements comprises an axis (31) that extends in the sagittal plane (S) by protruding on both sides of a bearing surface formed in the first plate, and in clearances (32) prepared in the second plate by openings in a spherical hole of the second plate.

7. Disk prosthesis according to claim 6, characterized in that the clearances (32) have a determined diameter to enable definition of the angular clearance of the relative rotation movements between the first and second plates.

8. Disk prosthesis according to claim 1, characterized in that the means of stop in relative rotation are formed by a female geometric shape (40) cooperating with a complementary male geometric shape (41), one of the geometric shapes being prepared on the first plate while the second geometric shape is prepared on the second plate.

9. Disk prosthesis according to claim 1, characterized in that the means of stop in lateral inflexion (12) are formed by a profile of the plates coming into contact with each other.

* * * * *